(12) United States Patent
Tathireddy et al.

(10) Patent No.: US 8,886,279 B2
(45) Date of Patent: Nov. 11, 2014

(54) HIGH ASPECT RATIO MICROELECTRODE ARRAYS ENABLED TO HAVE CUSTOMIZABLE LENGTHS AND METHODS OF MAKING THE SAME

(75) Inventors: Prashant Tathireddy, Salt Lake City, UT (US); Florian Solzbacher, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 413 days.

(21) Appl. No.: 12/996,356

(22) PCT Filed: Jun. 3, 2009

(86) PCT No.: PCT/US2009/046150
§ 371 (c)(1),
(2), (4) Date: Mar. 4, 2011

(87) PCT Pub. No.: WO2009/149197
PCT Pub. Date: Dec. 10, 2009

(65) Prior Publication Data
US 2012/0138335 A1    Jun. 7, 2012

Related U.S. Application Data

(60) Provisional application No. 61/058,310, filed on Jun. 3, 2008.

(51) Int. Cl.
*A61B 5/0478* (2006.01)
*A61N 1/05* (2006.01)

(52) U.S. Cl.
CPC ............ *A61N 1/0529* (2013.01); *A61N 1/0531* (2013.01)
USPC .............. 600/378; 29/825; 607/116; 600/544

(58) Field of Classification Search
USPC .................. 600/378, 377, 393, 544–545; 607/116–118; 29/825, 592.1
See application file for complete search history.

(56) References Cited

U.S. PATENT DOCUMENTS

| 4,685,466 A | 8/1987 | Rau |
| 4,837,049 A | 6/1989 | Byers et al. |

(Continued)

FOREIGN PATENT DOCUMENTS

| WO | WO 2005/072630 | 8/2005 |
| WO | WO 2006/055799 | 5/2006 |

OTHER PUBLICATIONS

Branner et al; Long Term Stimulation and Recording with a Penetration Microelectrode Array in Cat Sciatic Nerve; IEEE Transactions on Biomedical Engineering; vol. 51, No. 1; Jan. 2004.

(Continued)

*Primary Examiner* — Linda Dvorak
*Assistant Examiner* — Erin M Cardinal
(74) *Attorney, Agent, or Firm* — Thorpe North & Western LLP (57) ABSTRACT

A method of fabricating an array of micro electrodes enabled to have customizable lengths. A substantially criss-cross pattern of channels on a top surface of the work-piece substrate (10) is formed using electrical discharge machining to form a plurality of shaped columns (20) having tapered profiles. The shaped columns have a tapering profile which extends at least 50% of the length of the columns. The plurality of shaped columns is etched to sharpen the tapered tips into needle tips forming the array of microelectrodes.

16 Claims, 4 Drawing Sheets

(56) References Cited

U.S. PATENT DOCUMENTS

| | | | |
|---|---|---|---|
| 4,969,468 A * | 11/1990 | Byers et al. | 600/373 |
| 5,215,088 A | 6/1993 | Normann et al. | |
| 5,286,944 A | 2/1994 | Li | |
| 5,388,577 A * | 2/1995 | Hubbard | 600/377 |
| 5,457,041 A | 10/1995 | Ginaven et al. | |
| 5,472,592 A | 12/1995 | Lowery | |
| 5,591,139 A * | 1/1997 | Lin et al. | 604/264 |
| 5,656,414 A | 8/1997 | Chou et al. | |
| 5,689,603 A | 11/1997 | Huth | |
| 5,838,715 A | 11/1998 | Corzine et al. | |
| 5,895,562 A | 4/1999 | Dubin | |
| 6,091,975 A * | 7/2000 | Daddona et al. | 600/345 |
| 6,285,446 B1 | 9/2001 | Farhadiroushan | |
| 6,334,856 B1 | 1/2002 | Allen et al. | |
| 6,406,638 B1 | 6/2002 | Stoeber et al. | |
| 6,511,463 B1 | 1/2003 | Wood et al. | |
| 6,551,849 B1 | 4/2003 | Kenney | |
| 6,622,035 B1 * | 9/2003 | Merilainen et al. | 600/391 |
| 6,702,950 B2 | 3/2004 | Moon et al. | |
| 6,730,444 B2 | 5/2004 | Bowes | |
| 6,743,211 B1 | 6/2004 | Prausnitz et al. | |
| 6,782,283 B2 * | 8/2004 | Schmidt et al. | 600/372 |
| 6,815,360 B1 | 11/2004 | Canham et al. | |
| 6,896,850 B2 | 5/2005 | Subramanian et al. | |
| 6,980,282 B2 | 12/2005 | Choi et al. | |
| 7,027,874 B1 * | 4/2006 | Sawan et al. | 607/116 |
| 7,118,942 B1 | 10/2006 | Li | |
| 7,212,851 B2 | 5/2007 | Donoghue et al. | |
| 7,240,416 B2 | 7/2007 | Milojevic et al. | |
| 7,310,543 B2 * | 12/2007 | Smart et al. | 600/345 |
| 7,332,197 B2 | 2/2008 | Wood et al. | |
| 7,712,198 B2 | 5/2010 | Kuo et al. | |
| 7,951,300 B2 | 5/2011 | Bhandari et al. | |
| 7,991,475 B1 * | 8/2011 | Tang et al. | 607/45 |
| 2002/0082543 A1 | 6/2002 | Park et al. | |
| 2003/0208138 A1 | 11/2003 | Olson | |
| 2004/0048419 A1 | 3/2004 | Kitamura et al. | |
| 2004/0082875 A1 * | 4/2004 | Donoghue et al. | 600/544 |
| 2004/0267205 A1 | 12/2004 | Stemme et al. | |
| 2005/0011858 A1 | 1/2005 | Kuo et al. | |
| 2005/0137531 A1 | 6/2005 | Prausnitz | |
| 2005/0171480 A1 | 8/2005 | Mukerjee et al. | |
| 2006/0055090 A1 | 3/2006 | Lee et al. | |
| 2006/0110100 A1 | 5/2006 | Blauvelt et al. | |
| 2006/0127307 A1 | 6/2006 | Canham | |
| 2006/0135862 A1 * | 6/2006 | Tootle et al. | 600/373 |
| 2006/0173259 A1 * | 8/2006 | Flaherty et al. | 600/331 |
| 2007/0067007 A1 * | 3/2007 | Schulman et al. | 607/115 |
| 2007/0161964 A1 | 7/2007 | Yuzakov | |
| 2008/0102192 A1 | 5/2008 | Johnson et al. | |
| 2008/0125743 A1 | 5/2008 | Yuzhakov | |
| 2008/0138581 A1 | 6/2008 | Bhandari et al. | |
| 2008/0138582 A1 | 6/2008 | Bhandari et al. | |
| 2008/0138583 A1 | 6/2008 | Bhandari et al. | |
| 2008/0249391 A1 * | 10/2008 | Moxon et al. | 600/373 |
| 2008/0262416 A1 | 10/2008 | Duan et al. | |
| 2008/0275400 A1 | 11/2008 | Ferguson | |
| 2009/0011158 A1 | 1/2009 | Yeshurun | |
| 2009/0099534 A1 | 4/2009 | Lee et al. | |
| 2009/0283425 A1 * | 11/2009 | Clark et al. | 205/792 |
| 2009/0301994 A1 | 12/2009 | Bhandari | |
| 2010/0029148 A1 * | 2/2010 | Perlin et al. | 439/884 |
| 2010/0041972 A1 * | 2/2010 | Mason | 600/372 |
| 2012/0132613 A1 | 5/2012 | Bhandari | |

OTHER PUBLICATIONS

Campbell et al.; A Silicon-Based, Three Dimensional Neural Interface: Manufacturing Process for an Intracortical Electrode Array; IEEE; Aug. 1991; pp. 758-768; vol. 38, No. 8.

Clark et al.; DARPA Revolutionizing Prosthetics 2009; Making It Work: Animal Physiology & Device Testing; Dept. of Bioengineering University of Utah Jun. 28, 2007; 5 pgs.

Dhillon et al.; Residual Function in Peripheral Nerve Stumps of Amputees: Implications for Neural Control of Artificial Limbs; The Journal of Hand Surgery; 2004; pp. 605-615.

Rakwal et al; Fabrication of Compliant High Aspect Ratio Silicon Microelectrode Arrays Using Micro-Wire Electrical Discharge Machining; Microsyst Technol; 2009; pp. 789-797; vol. 15.

Fofonoff et al.; A Highly Flexible Manufacturing Technique for Microelectrode Array Fabrication in: [Engineering in Medicine and Biology, 2002; 24$^{th}$ Annual Conference and the Annual Fall meeting of the Biomedical Engineering Society] EMBS/BMES Conference; 2002; pp. 2107-2108.

Fofonoff et al.; Assembly-Ready Brain Microelectrode Array's in: Engineering in Medicine and Biology Society, Proceedings of the 25$^{th}$ Annual International Conference of the IEEE, 2003, pp. 1937-1940.

Jones et al.; A Glass/Silicon Composite Intracortical Electrode Array; Annals of Biomedical Engineering; 1992; pp. 423-437; vol. 20.

Tajadod et al.; Electophoretic Photoresist Application for High Topography Wafer Surfaces; International Conference on Compound Semiconductor Mfg; 2003; 4 pgs.

Tathireddy et al; Fabrication of 3-Dimensional Silicon Microelectrode Arrays Using Micro Electro Discharge Machining for Neural Applications; Proc. Transducer'09, 15th Int. Conf. on Solid-State Sensors, Actuators and Microsystems, Denver, CO, Jun. 21-25, 2009, pp. 1206-1209.

Tathireddy et al; Towards High Aspect Ratio Tungsten Micro Electrode Array for Neural Recording and Stimulation Applications; 13th Annual International Function Electrical Stimulation (FES) Society Conference, Freiburg, Germany, Sep. 21-25, 2008.

Tsung-Kuan et al.; Fabrication of Out-of-Plane Curved Surfaces in Si by Utilizing Rie Lag; IEEE; 2002; pp. 145-148.

Bhandari et al; A Novel Method of Fabrication Convoluted Shaped Electrode Arrays for Neural and Retinal Prostheses; Sensors and Actuators A; Nov. 4, 2007; pp. 123-130; vol. 145-146.

U.S. Appl. No. 12/464,691, filed May 12, 2009, Rajmohan Bhandari; office action dated Feb. 7, 2013.

U.S. Appl. No. 11/807,766, filed May 29, 2007, Rajmohan Bhandari; office action dated Feb. 19, 2013.

\* cited by examiner

HIGH ASPECT RATIO MICROELECTRODE ARRAYS ENABLED TO HAVE CUSTOMIZABLE LENGTHS AND METHODS OF MAKING THE SAME

RELATED APPLICATION

This application claims priority to U.S. Provisional Patent Application No. 61/058,310, filed Jun. 3, 2008, which is incorporated herein by reference.

FIELD OF THE INVENTION

The present invention relates generally to needle array devices and methods of fabrication. Accordingly, the present invention involves the fields of microscale fabrication, materials science, and process control.

BACKGROUND

Microelectrode arrays are used to stimulate and record electrical neuronal signals in the Central Nervous System (CNS) and Peripheral Nervous System (PNS). Sensory organs generate electrical signals that are transmitted by nerves to the brain. Nerves also conduct electrical signals from the brain to control muscular activity. Microelectrodes can be inserted into nerve tissue to record and stimulate electrical signals in various parts of the nerve tissue.

SUMMARY OF THE INVENTION

Figure 1:
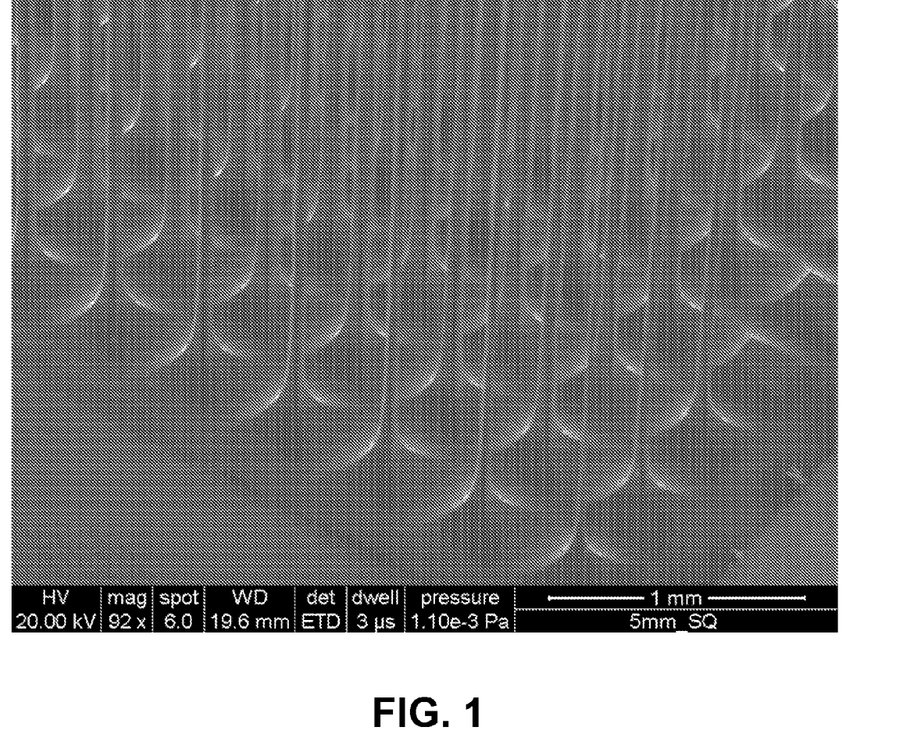
FIG. 1 is an SEM image of a UEA with high aspect ratio needles formed in accordance with conventional dicing and etching processing.

The ability to probe and stimulate neurons in complex three-dimensional environments is currently limited by the placement and lengths of electrodes. It has been recognized that longer electrodes would be useful in expanding options for research and neuro-prosthetic therapies. Unfortunately, merely using conventional electrode formation processes does not produce satisfactory needles when lengths are extended beyond about 1.5 to 2 mm (with a base footprint of 16 mm$^2$). FIG. 1 illustrates an attempt by the inventors to use standard Utah Electrode Array (UEA) processing to obtain ultra-high aspect ratio electrodes. As can be seen in this micrograph, several of the needles are either missing or have severe narrowing near the base making the electrodes which do survive etching extremely fragile. As such, the resulting arrays are not suitable for implanting and use.

The present invention includes a method of fabricating an array of microelectrodes enabled to have customizable lengths and high aspect ratios. The array of microelectrodes may be a three-dimensional electrical device adapted as a neural interface device or a cortical implant.

A method of fabricating an array of microelectrodes enabled to have customizable lengths. A substantially criss-cross pattern of channels on a top surface of the work-piece substrate is formed using electrical discharge machining to form a plurality of shaped columns having tapered tips. The tapered tips have a tapering profile which extends at least 50% of the length of the columns. The plurality of shaped columns is etched to sharpen the tapered tips into needle tips forming the array of microelectrodes.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

These drawings merely depict exemplary embodiments of the present invention they are, therefore, not to be considered limiting of its scope. It will be readily appreciated that the components of the present invention, as generally described and illustrated in the figures herein, could be arranged, sized, and designed in a wide variety of different configurations. Nonetheless, the invention will be described and explained with additional specificity and detail through the use of the accompanying drawings.

DETAILED DESCRIPTION

Before the present invention is disclosed and described, it is to be understood that this invention is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

It must be noted that, as used in this specification and the appended claims, the singular forms "a," "an," and "the" include plural referents unless the context clearly dictates otherwise. Thus, for example, reference to "a needle" includes one or more of such features, reference to "tips" includes reference to one or more of such ends, and reference to "machining" includes one or more of such steps.

Definitions

In describing and claiming the present invention, the following terminology will be used in accordance with the definitions set forth below.

As used herein, "substantial" when used in reference to a quantity or amount of a material, or a specific characteristic thereof, refers to an amount that is sufficient to provide an effect that the material or characteristic was intended to provide. Therefore, "substantially free" when used in reference to a quantity or amount of a material, or a specific characteristic thereof, refers to the absence of the material or characteristic, or to the presence of the material or characteristic in an amount that is insufficient to impart a measurable effect, normally imparted by such material or characteristic.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.6 mm to about 3 mm" should be interpreted to include not only the explicitly recited values of about 0.6 mm and about 3 mm, but also include individual values and sub-ranges within the indicated range. Thus, included in this numerical range are individual values such as 0.4 mm and 0.5 mm, and sub-ranges such as from 0.4-0.5 mm, from 0.35-0.4, etc. This same principle applies to ranges reciting only one numerical value. Furthermore, such an interpretation should apply regardless of the breadth of the range or the characteristics being described.

As used herein, the term "about" means that dimensions, sizes, formulations, parameters, shapes and other quantities and characteristics are not and need not be exact, but may be approximated and/or larger or smaller, as desired, reflecting tolerances, conversion factors, rounding off, measurement error and the like and other factors known to those of skill in the art. Further, unless otherwise stated, the term "about" shall expressly include "exactly," consistent with the discussion above regarding ranges and numerical data.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Embodiments of the Invention

The ability to probe and stimulate neurons in complex three-dimensional environments is currently limited by the placement and lengths of electrodes. It has been recognized that longer electrodes would be useful in expanding options for research and neuro-prosthetic therapies. Unfortunately, merely using conventional electrode formation processes does not produce satisfactory needles when lengths are extended beyond about 1.5 to 2 mm (with a base footprint of 16 $mm^2$). FIG. 1 illustrates an attempt by the inventors to use standard Utah Electrode Array (UEA) processing to obtain ultra-high aspect ratio electrodes. As can be seen in this micrograph, several of the needles are either missing or have severe narrowing near the base making the electrodes which do survive etching extremely fragile. As such, the resulting arrays are not suitable for implanting and use.

The present invention includes a method of fabricating an array of microelectrodes enabled to have customizable lengths and high aspect ratios. The array of microelectrodes may be a three-dimensional electrical device adapted as a neural interface device or a cortical implant. A substrate or substrate material may be used to fabricate the array of microelectrodes. The substrate is also referred to as a work-piece substrate to differentiate the substrate from a later used optional support substrate. The substrate material generally can be an electrically conductive material such as doped semiconductor material, metal, or combination thereof. Non-limiting examples of suitable materials include 'n' or 'p' type silicon, tungsten, titanium, platinum, iridium, stainless steel, steel, titanium nitride, a titanium-aluminum-vanadium alloy, tungsten carbide, copper, alloys thereof, or combination thereof.

Figure 2:
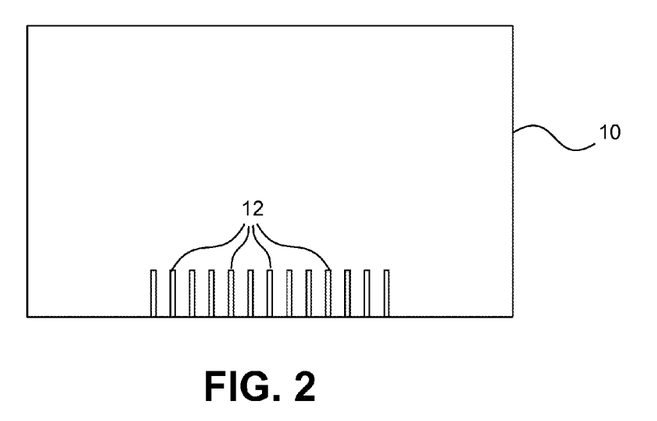
FIG. 2 is an illustration of a side view of rectangular channels formed by EDM in a work-piece substrate with the channels subsequently filled with a dielectric material in accordance with an embodiment.

In this method of array fabrication, a conductive work piece 10 is first electro discharged machined to form criss-cross rectangular channels 12 a fraction of millimeter deep on one surface (FIG. 2). A substantially criss-cross pattern of rectangular channels on the back surface of the work-piece substrate can be formed by dicing saw cuts or electrical discharge machining (EDM), although other machining techniques can be suitable (e.g. laser machining, deep reactive ion etching, etc). In one aspect, these back side cuts for the insulation lines can be performed using a dicing saw in order to prevent formation of a recast layer. EDM has a tendency to form a recast layer which reduces mechanical adhesion of insulating material such as glass to the silicon. In one aspect, the dicing saw can be a wafer cutting saw (e.g. Disco DAD685, K&S Dicing Saw Model 982-6) capable of making cuts up to 1 mm deep and up to 100 µm wide.

In one aspect, a criss-cross pattern can be a first series of parallel lines or channels that are substantially perpendicular to a second series of parallel lines or channels, although skewed or other non-perpendicular cuts can be made as long as an array of columns are formed. Accordingly, the cross-sectional shape of the columns can often be square, although rectangular, triangular, hexagonal, etc. can also be formed. EDM includes removing work-piece substrate material from a specified patterned area or location of the work-piece substrate using electricity. In an EDM process, material is removed by a series of rapidly recurring electric arcing discharges between an electrode (the cutting tool) and the work-piece substrate. Although rectangular channels are specifically mentioned, any geometric shape (e.g., polygon) that can be formed into a column may be formed on the back surface of the work-piece substrate. Typically, the channels on the back surface can be relatively shallow. As a non-limiting guideline, the back-side channels can generally range from about 100 µm to about 1 mm in depth. In one aspect, arrays with wider pitch (distance between electrodes) can also be formed such that even deeper channels can be formed on the back side.

After the rectangular channels are formed in the back surface of the work-piece substrate, the rectangular channels can be filled with a dielectric material to insulate the conductive electrodes or probes from each other. The channels created by dicing or other suitable machining are then filled with a dielectric material (e.g. glass frit, epoxy, etc.). Although other materials can also be used, the dielectric material can be glass when silicon is used as the conductive material in the work-piece substrate, or the dielectric material can be epoxy when metal is used as the conductive material in the work-piece substrate. Generally, any insulating material can be used such as, but not limited to, glass, epoxy, adhesives, or the like.

Figure 3:
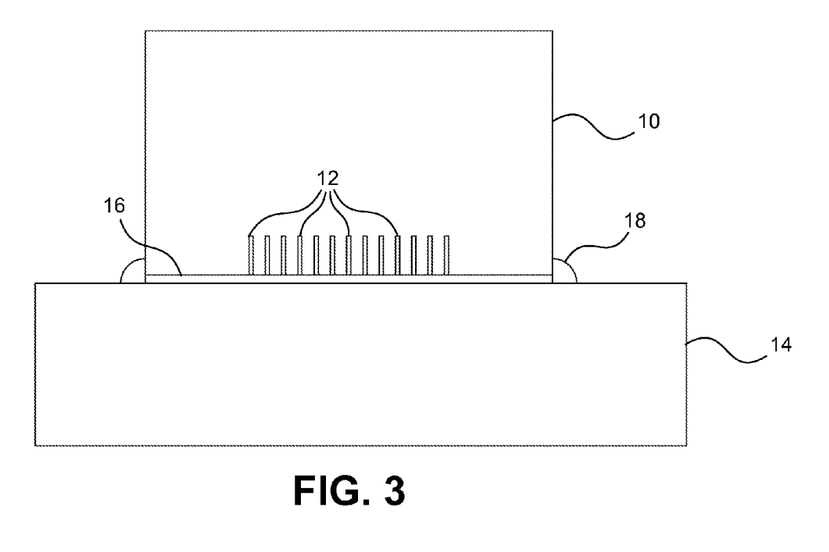
FIG. 3 is an illustration of a side view of a work-piece substrate mounted on a conductive support substrate using removable conductive material in accordance with an embodiment.

The next step is to mount the work piece 10 on a conductive support substrate 14 using a temporary, highly conductive material 16 with the rectangular channels facing the support substrate (FIG. 3). The back surface of the work-piece substrate can be mounted on a top surface of a support substrate with the conductive material sandwiched between the work-piece substrate and the support substrate. The support substrate can be part of the EDM machine or a conductive member associated therewith. The conductive material sandwiched between the work-piece substrate and the support substrate can be an epoxy, removable tape or the like.

The back surface of the work piece can optionally be further secured or mounted on the top surface of the support substrate with an epoxy on a perimeter interface 18 of the work-piece substrate and the top surface of the support substrate. The perimeter interface can be the outer edge of the back surface of the work piece in contact with the top surface of the support substrate or the conductive material sandwiched between the work-piece substrate and the support substrate. Alternatively, if a conductive material is sandwiched between the work-piece substrate and support substrates, the material (e.g. epoxy) does not have to conductive. In another embodiment, the perimeter interface can be the outer edge of the back surface of the work piece adjoining other sides (e.g., perpendicular sides). The epoxy on the perimeter interface can be conductive. The epoxy can be continuously formed on the perimeter interface or can be formed in a plurality of locations on the perimeter interface so that each location has a defined length or bead of epoxy less than the entire perimeter interface. In other words, the epoxy on the perimeter interface can optionally be discontinuous. Although other conductive supports can be suitable, non-limiting examples can include metal (copper, aluminum etc.) stage/blocks.

Figure 4:
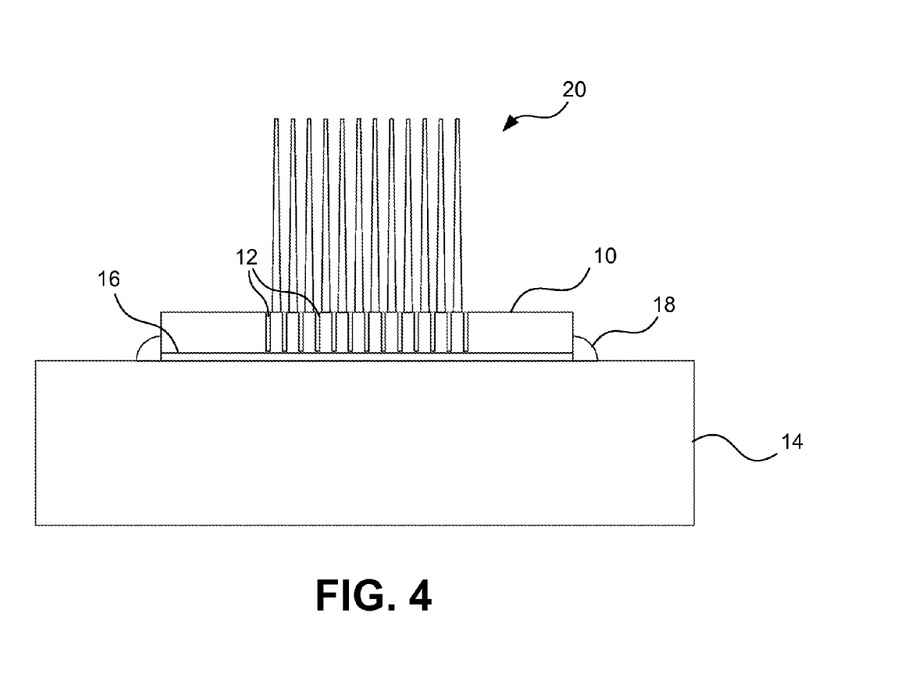
FIG. 4 is an illustration of a side view of an array of electrodes having tapered tips formed by EDM in accordance with an embodiment.

The array of ultra high aspect ratio columns/pyramids can be machined using EDM. Referring to FIG. 4, the array of tapered columns 20 can be machined such that the new cuts fall on top of the dielectric material 12 to form electrically isolated array of electrodes/pyramids mechanically held together at the bottom by the dielectric material. Using this technique, the aspect ratio is limited only by the material (work piece) strength and properties. The advantage of this technique over the state of the art is the capability of producing pyramid like structures for what would finally be sharp needle electrodes. A substantially criss-cross pattern of channels on a top surface of the work-piece substrate may be formed by EDM to form a plurality of shaped columns having tapered electrodes. The tapered region of the column is most often from about 50 to about 100% of the column length, although at least 90% can also be suitable. In one aspect, the tapered region, or tapering profile, can extend substantially to the base of the column as shown in FIG. 4. The tips of the tapered electrodes can be of width between 20 to 50% of the base width. The tapered profile can generally be a substantially linear taper from the tip to the opposite end of the taper. EDM cuts do not have go all the way to the bottom, e.g. touching the glass. More specifically, EDM needs conductive material to machine such that when it hits the glass or non-conductive insulator, the wire can break in some cases. Thus, channel cuts can safely be as high as 50 μm from the bottom/glass, and the remaining material can be removed during etching.

In one aspect, the aspect ratio of the columns can range from about 1 to about 20, and in one aspect from about 1 to about 5. Thus, in one aspect, the aspect ratio can correspond to ultra-high aspect ratio column, e.g. about 10 to about 20. This approach can dramatically reduce the volume of material to be etched/removed during later processes, and thereby allow easier etchant access to the deeper regions of the columns. The columns may be rectangular, triangular, circular, or other geometric shape (e.g., polygon) that can be formed into a column. Ultra high aspect columns and/or pyramids may be formed by EDM. In one aspect, the EDM process can be micro-EDM such that the wire has a wire diameter in the micron range. In another aspect, the micro-EDM can utilize a wire diameter from 30 μm to about 40 μm.

In one alternative aspect, the tapered columns can be formed in a two stage EDM process. A first rough step can be used, followed by a second finishing step. Typically, the rough step can be accomplished by using a relatively higher pulse off time and higher electrical powers and the finishing step using a relatively lower pulse off time and lower powers. The cutting speed in the first step is generally much faster than the second due to lower power parameters. In one specific example, a rough EDM step uses a pulse off time of about 42.5 μsec, pulse on time of 4.5 μsec and a cutting speed of 1.74 mm/minute while the finishing EDM step uses a pulse off time of 12.5 μsec and pulse on time of 52.4 μsec. The use of two stages allows for removal of machining debris and reduction of the recast layer from the rough step and results in a reduction in surface roughness.

Figure 5:
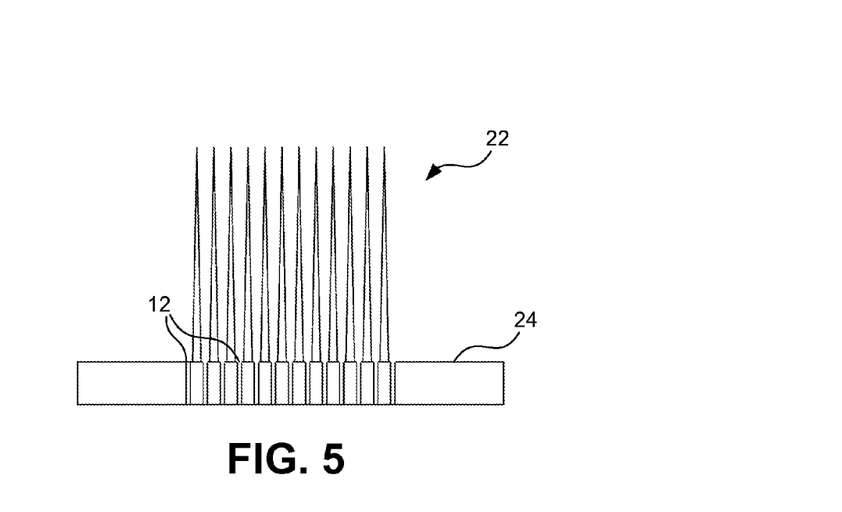
FIG. 5 is an illustration of a side view of an array of electrodes having tapered tips etched to sharpen the electrodes in accordance with an embodiment.
Figure 6:
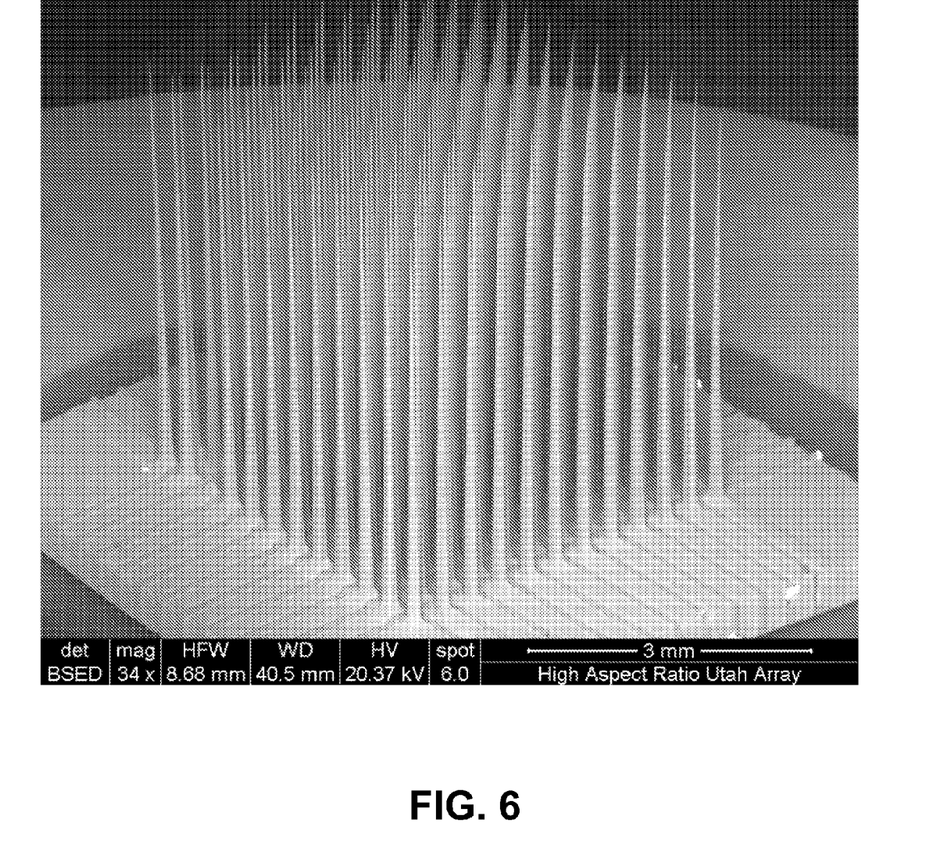
FIG. 6 is a SEM perspective image of an array of electrodes formed in accordance with one embodiment.

Such structures also allow easier processing to form needles because they significantly reduce the volume of material to be etched during the etching process and also allow easier etchant access and flushing in the deeper regions of the columns. In the last step, the array of columns is etched to form array of sharp, high aspect ratio needles 22 as shown in FIG. 5. FIG. 6 is an SEM of an etched high aspect ratio array formed in accordance with one embodiment of the present invention. In this example, the needles have a substantially uniform taper profile from the base to the tip. These needles thus have a high mechanical strength and can be injected into tissue with minimal breakage under standard injection techniques. The disclosed method allows fabrication of ultra high aspect ratio arrays for use to access deeper areas of cortex and complete coverage of nerves for recording and stimulating applications.

The plurality of shaped columns can be etched to sharpen the tapered tips into needle tips to form the array of microelectrodes. The etching of the shaped columns can use an etchant solution. The etchant solution can be a chemical etchant, an electrochemical etchant, or combination thereof. Examples of suitable chemical etchants for silicon and most metal based arrays can include $HF(5\%\ v/v)+HNO_3(95\%\ v/v)$, $HF+HNO_3+CH_3COOH$, $HF+HNO_3+CH_3COOH+H_2O$, and for metal only $H_2SO_4+H_2O_2$, $KOH+K_3Fe(CN)_6+H_2O$, etc., although others can be used. Non-limiting examples of suitable electrochemical etchants can include $KNO_3$, $KNO_3+H_2O_2$, NaOH etc. In one aspect, the etching can be substantially static, e.g. no mixing or agitation. Typically, etch time can be sufficient to achieve a substantially uniform profile needle without compromising structural integrity of the needles. For example, too short an etch time can leave the needles blocky which can reduce penetration and/or increase tissue damage upon insertion. On the other hand, excessively long etch times can result in fragile needles or complete dissolution of needles. Although etch times can vary based on dimensions of the columns and etchant composition and conditions, as a general etch times can vary from about 1 minute to about 180 minutes (e.g. longer times tend to be desirable for electrochemical etching depending on the parameters used. A sonicator can be used to accelerate the diffusion of ions in an etchant solution. In one aspect, an electrochemical etching resulted in good results where shapes of the needles are affected by etching conditions. For example, a higher frequency (up to 80 Hz) produced more conical shapes and higher currents while lower frequencies (~5-40 Hz) tended to maintain original cross-sectional shape. Higher voltages tend to produce convex shapes under limited ion diffusion. Temperatures also play role in the surface finish and shapes of the electrodes. Higher temperatures up to 80° C. can help reduce the electrochemical etching time.

Upon completion of the needles via etching, a suitable solvent such as acetone, xylene, isopropyl alcohol, or sequence of such solvents can be used to dissolve the conductive material or tape sandwiched between the work-piece substrate and the support substrate used to mount the work-piece substrate to the support substrate. Solvents can also be used to remove the epoxy on the perimeter interface. Acetone can used to remove the work-piece substrate from the support after the array of microelectrodes has been formed.

Although heights can vary depending on the application, the height of the shaped columns of the ultra high aspect array of microelectrodes may be between 1.5 mm and 2 cm. In another embodiment, the height of one of the shaped columns may be between 3 mm and 10 mm with a distance between shaped column tips from 100 µm to 1 mm. The height of a microelectrode shaped column can be the distance between the top point of a column and the deepest part of the trench between columns created by the EDM process and etching. In one aspect, the spacing between adjacent shaped columns is from 50 µm to 150 µm at a base of the shaped column before etching. The spacing between adjacent shaped columns can be the width of material removed at the base between two columns. The shaped column can have a column length and a column width between 50 µm and 250 µm at a base of the shaped column before etching when the column shape is rectangular or square. The shaped column can have a column diameter between 50 µm and 250 µm at a base of the shaped column before etching when the column shape is circular. The column can be the substrate material remaining after the machining process and subsequent etching.

The heights of the shaped columns of the ultra high aspect array of microelectrodes can vary between adjacent shaped columns or can be substantially uniform across the array. In one aspect, the height variation between two adjacent shaped columns can be up to 10% of the length of the longest electrode in an array.

A three-dimensional array of microelectrodes can be formed using the method above. The three-dimensional array of microelectrodes can have a base of rigid material. The array of microelectrodes can have a plurality of shaped electrically conductive columns having tapered tips protruding from the base. Each shaped electrically conductive column can be electrically isolated from each other at the base by a dielectric material, and a height of one of the shaped columns is between 1.5 mm and 2 cm with a distance between tips of the shaped electrically conductive columns from 100 µm to 1 mm. In another embodiment, the height of one of the shaped columns can be between 3 mm and 10 mm.

These electrode arrays can be further processed to form various devices and/or features as described elsewhere. As a brief example, additional processing can include flip-chip bonding, formation of power coils, logic circuits, wireless communication, encapsulation, and the like.

The present method is a new technique to fabricate ultra high aspect ratio electrode array. Such a penetrating array can access deeper areas of nerves and cortex for neural signal recording and stimulation. The conventional technology is only capable of producing relatively low aspect ratio electrodes. The disclosed method allows fabrication of ultra high aspect ratio arrays with customizable lengths for use to access deeper areas of cortex and complete coverage of nerves for recording and stimulating applications.

It is to be understood that the above-referenced arrangements are illustrative of the application for the principles of the present invention. Numerous modifications and alternative arrangements can be devised without departing from the spirit and scope of the present invention while the present invention has been shown in the drawings and described above in connection with the exemplary embodiment(s) of the invention. It will be apparent to those of ordinary skill in the art that numerous modifications can be made without departing from the principles and concepts of the invention as set forth in the claims.

What is claimed is:

1. A method of fabricating an array of microelectrodes enabled to have customizable lengths, comprising:
   a) providing a substantially non-metal work-piece substrate;
   b) forming a substantially criss-cross pattern of channels on a top surface of the substantially non-metal work-piece substrate to form a plurality of tapered columns each shaped by electrical discharge machining (EDM) to have a tapered tip and a base, wherein the tapered tips have a tapering profile which extends at least 50% of a height of the tapered columns; and
   c) etching the plurality of tapered columns with an etchant capable of etching non-metals to sharpen the tapered tips into needle tips to form the array of microelectrodes.

2. The method of claim 1, further comprising:
   a) forming a second substantially criss-cross pattern of rectangular channels in a back surface of the substantially non-metal work-piece substrate; and
   b) filling the rectangular channels with a dielectric material prior to mounting the back surface of the substantially non-metal work-piece substrate on a top surface of a support substrate.

3. The method of claim 2, wherein the forming the second pattern in the back surface is accomplished using a dicing saw prior to forming the substantially criss-cross pattern of channels on the top surface of the substantially non-metal work-piece substrate.

4. The method of claim 2, wherein the substantially non-metal work-piece substrate comprises Si and the dielectric material comprises a glass.

5. The method of claim 1, further comprising mounting a back surface of the substantially non-metal work-piece substrate on a top surface of a support substrate with a conductive material sandwiched between the substantially non-metal work-piece substrate and the support substrate.

6. The method of claim 5, wherein mounting the back surface of the substantially non-metal work-piece substrate on the top surface of the support substrate further comprises adhering the substantially non-metal work-piece substrate to the support substrate with an epoxy on a perimeter interface of the substantially non-metal work-piece substrate and the top surface of the support substrate.

7. The method of claim 6, wherein the epoxy is a conductive material.

8. The method of claim 1, wherein the forming of the tapering profile includes a two-step EDM process of a first rough cut step and a second finishing step.

9. The method of claim 1, wherein the height of one of the tapered columns is between 1.5 mm and 2 cm with a spacing between adjacent tapered columns from 50 µm to 150 µm at the base of the tapered columns before etching.

10. The method of claim 1, wherein the plurality of tapered columns have an aspect ratio from about 10 to about 20.

11. The method of claim 1, wherein the tapering profile extends at least 90% of the height.

12. The method of claim 11, wherein the tapering profile extends substantially to the base.

13. The method of claim 1, wherein forming the channels on the substantially non-metallic work-piece substrate creates at least two adjacent tapered columns of varying heights.

14. The method of claim 1, wherein the etchant capable of etching non-metals is an etchant solution selected from the group consisting of a chemical etchant, an electrochemical etchant, and combination thereof.

15. A three-dimensional array of microelectrodes formed by the method of claim 1 wherein:
   the substantially non-metal work-piece substrate is further a rigid material; and
   the tapered columns are electrically conductive columns which are electrically isolated from each other at the bases by a dielectric material, and wherein a height of one of the tapered columns is between 1.5 mm and 2 cm with a distance between tips of the tapered columns from 100 µm to 400 µm.

16. The three-dimensional array of microelectrodes of claim 15, wherein the tapering profile extends at least 90% of the height.

* * * * *